United States Patent
Allain et al.

(10) Patent No.: US 9,839,724 B2
(45) Date of Patent: Dec. 12, 2017

(54) SYSTEM AND STENT FOR REPAIRING ENDOVASCULAR DEFECTS AND METHODS OF USE

(71) Applicants: Purdue Research Foundation, West Lafayette, IN (US); The Henry M. Jackson Foundation for the Advancement of Military Medicine, Inc., Bethesda, MD (US)

(72) Inventors: Jean Paul Allain, West Lafayette, IN (US); Lisa Reece, Lafayette, IN (US); Zhangcan Yang, West Lafayette, IN (US); Rocco Armonda, Bethesda, MD (US); Ravindra Kempaiah, West Lafayette, IN (US); Teodoro Tigno, Gaithersburg, MD (US)

(73) Assignees: Purdue Research Foundation, West Lafayette, IN (US); The Henry M. Jackson Foundation for the Advancement of Military Medicine, Inc., Bethesda, MD (US)

(*) Notice: Subject to any disclaimer, the term of this patent is extended or adjusted under 35 U.S.C. 154(b) by 0 days.

(21) Appl. No.: 15/464,298

(22) Filed: Mar. 20, 2017

(65) Prior Publication Data
US 2017/0189584 A1 Jul. 6, 2017

Related U.S. Application Data

(63) Continuation of application No. 14/349,865, filed as application No. PCT/US2012/059151 on Oct. 6, 2012, now abandoned.

(60) Provisional application No. 61/544,104, filed on Oct. 6, 2011.

(51) Int. Cl.
| | |
|---|---|
| A61F 2/06 | (2013.01) |
| A61L 31/08 | (2006.01) |
| A61F 2/07 | (2013.01) |
| A61F 2/86 | (2013.01) |
| A61L 31/16 | (2006.01) |
| A61F 2/95 | (2013.01) |

(52) U.S. Cl.
CPC .............. *A61L 31/082* (2013.01); *A61F 2/07* (2013.01); *A61F 2/86* (2013.01); *A61L 31/16* (2013.01); *A61F 2/95* (2013.01); *A61F 2210/009* (2013.01); *A61L 2300/64* (2013.01); *A61L 2400/18* (2013.01); *A61L 2420/08* (2013.01)

(58) Field of Classification Search
CPC .................................. A61L 31/10; A61L 31/16
USPC .................................. 623/1.15, 1.42
See application file for complete search history.

*Primary Examiner* — Thomas J Sweet
*Assistant Examiner* — Tiffany Shipmon
(74) *Attorney, Agent, or Firm* — Valauskas Corder LLC

(57) ABSTRACT

Disclosed are endovascular stents in which a portion of the stents have a bioactive coating for promoting repair of damaged vessels, systems comprising the stents, and methods of using the stents to promote occlusion of aneurysms and/or repair damaged vessels.

16 Claims, 2 Drawing Sheets

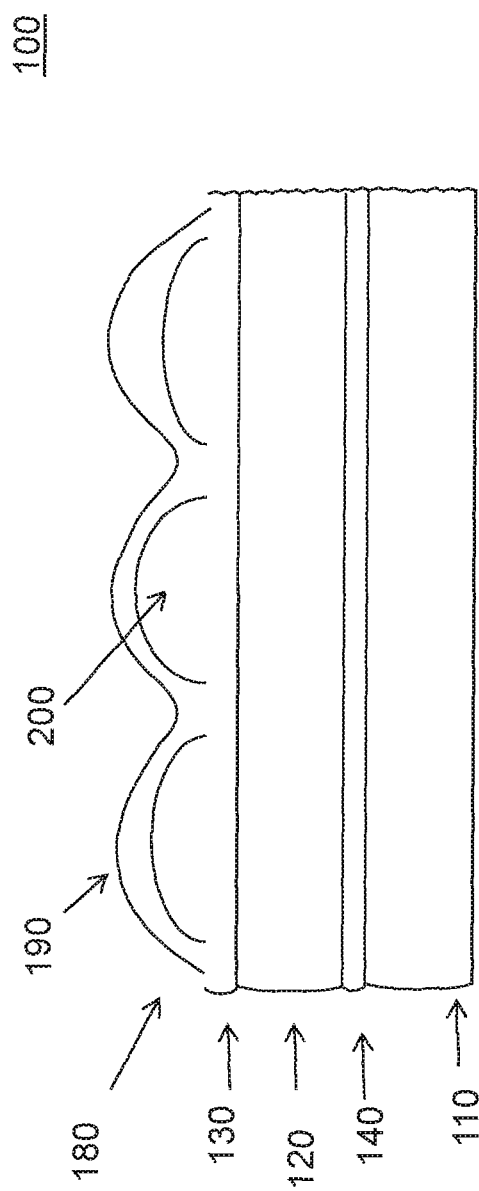

SYSTEM AND STENT FOR REPAIRING ENDOVASCULAR DEFECTS AND METHODS OF USE

CROSS-REFERENCE TO RELATED APPLICATIONS

This is a continuation application of U.S. patent application Ser. No. 14/349,865, filed Apr. 4, 2014, which is a National Stage Application under 35 U.S.C. §371 of International Application No. PCT/US2012/059151, filed Oct. 6, 2012, which claims the benefit of U.S. Provisional Application No. 61/544,104, filed Oct. 6, 2011, which are herein incorporated by reference in their entireties.

STATEMENT REGARDING FEDERALLY SPONSORED RESEARCH OR DEVELOPMENT

This invention was made with government support under Grant No. W81XWH-11-2-0067 awarded by the Army Medical Research and Material Command, The United States Government has certain rights in this invention.

FIELD OF THE INVENTION

The invention relates generally to a system, vascular stents and methods of repairing endovascular defects. More particularly, the present invention relates to a system, vascular stents, and methods for treating injured or defective blood vessels, including aneurysms, such as neurovascular aneurysms. The vascular stent employed in the system and methods of the invention includes a bioactive coating for use in treatment of injured or defective blood vessels, including intracranial or cerebral aneurysms.

BACKGROUND OF THE INVENTION

An aneurysm is an abnormal bulging or ballooning of an artery due to a weakness in the arterial wall. Intracranial or cerebral aneurysms, which occur in approximately 2% of the population, are frequently life-threatening when rupture occurs. Conventional treatment includes surgical clipping to bypass the aneurysm and endovascular coiling of the aneurysm. Endovascular coiling involves packing the aneurysm with small platinum coils to cause embolization of the aneurysm. Endovascular coiling has the advantage of being less invasive than surgical repair of intracranial aneurysms, because the coils are delivered by a catheter inserted into a femoral artery of the patient, Although endovascular coiling has been effective in the treatment of narrow neck aneurysms, it is less effective in treating wide neck aneurysms. The irregular interface between the coil mass and the parent artery increases the risk of thrombosis leading to stroke, especially in wide neck aneurysms, Further, because filling the aneurysm sac with coils does not address the diseased parent artery segment, there remains a high risk of regional recurrence of an aneurysm. Stents have been used in stent-assisted coiling in the treatment of patients with wide-necked intracranial aneurysms to maintain the coils in place and to maintain the patency of the affected artery. However, stent-assisted coiling in the treatment of wide neck aneurysms is problematic due to challenges associated with the anatomical reconstruction of a large segmental parent artery defect and impaired durability of the affected vessel.

Ionita et al. described the use of a variable porosity stent with a low porosity patch that covers the aneurysm neck as a primary treatment of intracranial aneurysms (Ionita et al., 2009 Stroke 40:959-965). The variable porosity stents of Ionita, referred to as asymmetric vascular stents (AVS), were used to treat aneurysms in rabbits. Each of the nine rabbits treated with AVS showed complete occlusion of the aneurysm; however, three of the nine rabbits died subsequent to AVS treatment.

There is a need in the art for systems, stents, and methods of treating aneurysms that reduce inflow of blood from the aneurysm to the parent artery while minimizing risk of thrombogenic occlusion of the parent artery and/or heal the damaged vessel. The present invention satisfies that demand.

SUMMARY OF THE INVENTION

In one embodiment, the present invention includes an endovascular stent for use in repairing an injured, damaged, or defective blood vessel. The stent has the advantage of being suitable for occluding aneurysms and/or repairing damaged vessels.

The stent may be delivered to the site of the vessel in need of treatment by catheterization, e.g., via the femoral artery. Thus, in the treatment of intracranial vessel damage, e.g., cerebral aneurysms, the stents and methods of treatment using those stents, are minimally invasive compared to surgical methods of repair.

The stent of the invention is designed to have a coating on a portion of the stent surface. The coating includes a magnetic material deposited on portion of an outer surface of the stent, an ion-beam nanostructured biocompatible layer, and a bioactive layer formed on the biocompatible layer. The bioactive layer comprises PCSM.

In certain embodiments, the stent includes an underlayer between the stent surface and the magnetic layer in order to promote better adhesion of top layers.

Advantageously, the magnetic region may be made of any suitable material, including a metal layer, or a biopolymer impregnated with a magnetic metal.

In certain embodiments, the stents may also include nanoscale particles imbedded in the coating to facilitate radiation-enhanced tomography.

The stents were designed for treatment of intracranial aneurysms, in particular wide neck aneurysms.

In another embodiment is provided a system for delivering a stent to a —a cerebral artery comprising an endovascular catheter, the stent of the invention, and magnetized cells. Interaction of the magnetized cells with the magnetized coating directs cells that promote healing and regrowth of damaged vessels to a targeted region.

In another embodiment are provided methods of repairing a cerebral artery and/or occluding an aneurysm by delivering the stent of the invention to the cerebral artery comprising the aneurysm, such that the portion of the stent comprising the coating is proximal to the neck of the aneurysm.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which:

FIG. 2 illustrates an embodiment of the stent bioactive coating of FIG. 1.

DETAILED DESCRIPTION OF EMBODIMENTS OF THE INVENTION

The embodiments disclosed below are not intended to be exhaustive or limit the disclosure to the precise forms disclosed in the following detailed description. Rather, the embodiments are chosen and described so that others skilled in the art may utilize their teachings.

In one embodiment, the present invention provides stents for use in the treatment of intracranial or cerebral aneurysms. A portion of the stent designed for placement proximal to the neck of the aneurysm comprises a bioactive stent coating. The bioactive stent coating includes a magnetic portion for attracting magnetized cells.

This disclosure includes a minimally invasive protocol for treatment of cerebral aneurysms. Endovascular surgical treatment makes use of a catheter-based stent deployment to the patient. A bioactive stent coating prototype therefore is used that combines magnetic protocol for cell attraction with surface ion-beam driven nanopatterning for cell regulation at the molecular and cellular scale.

This protocol would allow for a fast-endovascular treatment, minimizing cerebral trauma and prompt reconstructing of the aneurysmal neck defect. Reconstruction of the aneurysmal neck defect requires control of cell function at the molecular level.

This is the first technique to exploit nanoscale ($10^{-9}$ m) to mesoscale topography and control to regrow tissue at the neck orifice of a cerebral aneurysm. Mesoscale is general defined as of intermediate size. For this disclosure mesoscale generally refers to length scales from nanoscale to approximately microscale ($10^{-79}$ m). In particular, this treatment seeks to exploit bioactive coatings that attract cells to that region asymmetrically and promote tissue growth by manipulating nanopatterned surface on the coating.

In certain embodiments, a partially coated or asymmetrically coated stent according to the present disclosure includes a region rendered magnetic to locally attract biological cells, the magnetic region coupled with ion-beam nano-structured bio-compatible coating for tissue proliferation thus promoting healing, and use of porcine coronary smooth muscle (PCSM) as nidus or locus for cell recognition, for effective membrane repair, expeditious endothelialization and enhanced durability in a pulsating blood environment, for example, near the aneurysmal neck region. By combining a biocompatible multi-functional stent coating facing the aneurysmal neck defect, attraction of magnetic or magnetized cells can be locally manipulated and rapidly promote tissue growth reconstructing the absent tunica media.

Figure 1A:
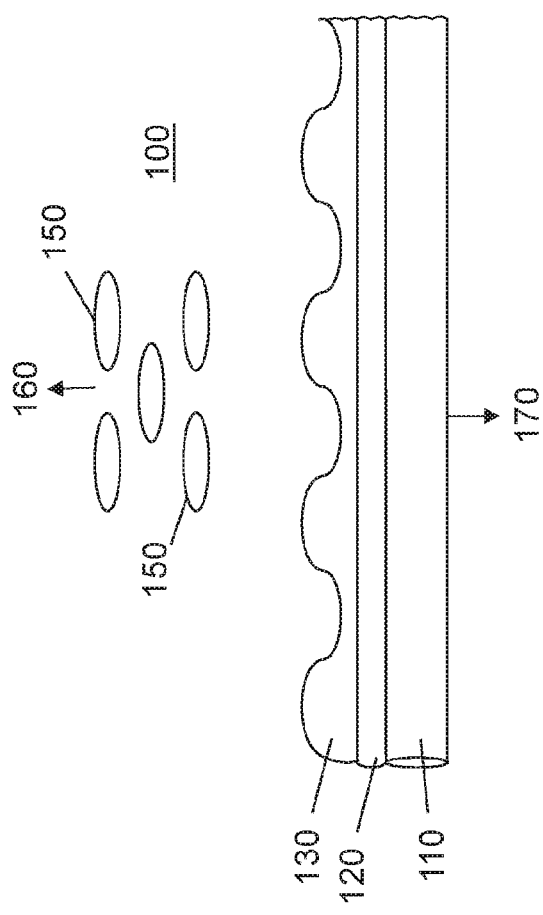
FIG. 1A shows a cross-section of an embodiment of a stent having a bioactive coating on an abluminal surface of the stent.

One embodiment of the invention is depicted in FIG. 1A, which shows a cross section of a stent portion 100 having a bioactive stent coating according to the present invention. A stent wall surface 110 is coated with a nickel layer 120, having a gold layer 130 nanopatterned over the nickel layer 120, facing the abluminal side 160. The uncoated side of the stent wall 110 faces the luminal side 170. A plurality of magnetized endothelial cells 150, such as HUVEC cells is proximal to the abluminal side 160 of the stent portion 100. The stent portion 100 of the stent is positioned such that the portion having the bioactive stent coating 100 is facing the neck of the aneurysm. In certain embodiments, the stent has variable porosity, with a less porous portion that is positioned over the aneurysm neck region to induce stasis and subsequent thrombosis within the aneurysm. In general, the bioactive coating is fabricated asymmetrically over only the portion of the stent that will span face the aneurysm neck region, facing the aneurysm. The purpose for the asymmetric coating design is to confine the induced thrombogenic activity to the aneurysm.

Figure 1B:
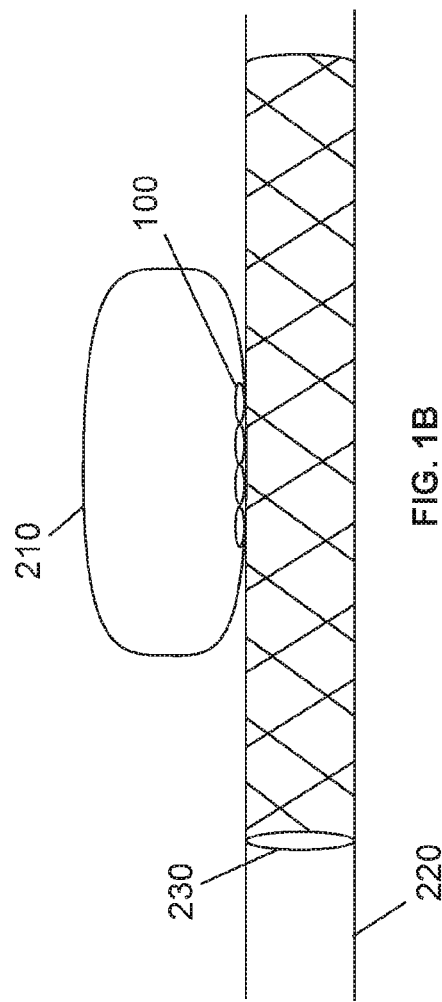
FIG. 1B depicts a vessel with an aneurysm containing a stent having a bioactive coating the abluminal surface facing the aneurysm.

FIG. 1B illustrates a vessel 220 having an aneurysm 210 with a stent 230 placed in the lumen of the vessel 220. The stent 230 includes a stent portion 100 as described above. The stent 230 is positioned within the vessel 220 so that the stent portion 100 is proximal to the neck region of the aneurysm 210. The porosity of the stent portion 100 is lower than the porosity of the remainder of the stent 230.

With reference to FIG. 2, in certain embodiments, a stent according to the present invention includes a stent portion 100 in which the stent wall surface 110, which is made of a material such as titanium, Nitinol, or SS316, comprises an underlayer 140 to support adherence of top layers to the stent surface. The underlayer is made of a material such as Cr. A layer 120 such as nickel, rendered magnetic to locally attract biological cells, overlays the underlayer. The magnetic layer 120 is coupled to a bio-compatible coating 180 which includes an ion-beam nano-structured coating 130 made from a material such as gold and a bioactive layer 190. The ion-beam nano-structured coating 130 includes nanostructures such as nano islands 200. The bioactive layer 190 includes PCSM. The bio-compatible coating aids in tissue proliferation to promote healing, and PCSM functions as nidus for cell recognition.

Any stent suitable for vascular repair may be used in the stents and methods of the invention. Examples of suitable stents include, without limitation, titanium stents, Nitinol stents, and SS316 stents. A region of the stent is rendered magnetic to locally attract biological cells. In certain embodiments, this is accomplished by coating a magnetic film on the stent in the portion that will face the aneurysm neck region using electroplating. In certain embodiments, the magnetic film has a thickness in the range of about 0.5-μm to about 10-μm. An underlayer (e.g. Cr) is deposited to adhere the top layers to the stent surface material (e.g., Ti, Nitinol or SS316) using magnetron sputtering. In another embodiment, the stent may be rendered magnetic using magnetic bacterial nanocellulose (MBNC), a unique biopolymer, which can be used as scaffold for initial endothelial cell attraction and attachment. Bacterial nanocellulose (BNC) can be made magnetic by impregnation of candidate magnetic nanoparticles. Magnetic nanoparticles including cobalt-ferrite and ferrite complex nanoparticles were synthesized and used to impregnate the BNC matrix to form MBNC. The MBNC was evaluated for the ability to attract magnetically loaded endothelial cells in a simulated vascular environment using a custom designed microfluidic flow device.

The matrix of BNC material can be loaded with various nanoparticles like silver, ferric complexes, cobalt ferrite nanoparticles and organic moieties. Triplets of BNC pellicles were grown at various pH conditions. It was found that pH 5 yields the optimal result. The magnetic properties of the MBNC have been established. The MBNC will be coupled to stents. Initial BNC films were prepared by culturing the bacterial strain Glucanocetobacter xylinus (Cat.#53524, ATCC, Manassas, Va.) as follows, A primary culture was formed by inoculating sterile Hestrin and Schramm media (containing D-glucose, 2.0% w/v, peptone, 0.5% (w/v); yeast extract, 0.5% (w/v), disodium phosphate, 0.27% (w/v), citric acid, 0.115% (w/v), (pH 5.0). The bacteria were first inoculated (primary inoculation, before homogenization) in the Hestrin-Schramm media and used for primary inoculation with solid agar. The culture was incubated at 30° C. for 3 days in an incubator maintained at specific oxygen and moisture content. Pellicles were formed at the interface of air/culture medium and were harvested on day three. The leathery pellicles were removed and treated with 1 N NaOH solution at 75° C. for 20 minutes. The pellicles were rinsed with Millipore water three times to remove the residual bacteria. The purified BNC pellicles were freeze-dried before further magnetic functionalization. The stents of the invention are delivered to the aneurysmal neck defect by catheterization. Stent implantation alters the hemodynamic flow behavior near the aneurysm neck orifice, thus leading to occlusion of the aneurysm. Catheterization will be used to deliver nidus cells directly to the aneurysm neck orifice, with the cells attracted to the magnetic stent region. The velocity profile and flow domain of the blood flow changes significantly around the aneurysm neck orifice due to the aneurysm and implantation of the stent. This modified flow pattern has been well studied. It has been reported that that implantation of stents reduces the intra-aneurysmal flow velocity of middle cerebral artery (MCA) aneurysms by about 43-64% affecting flow structure in the domes. The primary cause for these changes is the increased resistance to flow though the stent pores into the aneurysmal sac. The delivery of cells by catheterization, reduction of flow velocity, and the vortex around the stent result in a decrease in drag force acting on the endothelial cells and as a result, a magnetic coating having a thickness of several micrometers coating is sufficient to attract cells to the stent surface.

The cells can be magnetically labeled or magnetized using commercially available superparamagnetic iron oxide nanoparticles (MNP). Quantum dots (QDs) be used to label micelles. In certain embodiments, endothelial cell lines available commercially may be magnetically labeled for use in the methods of the invention. In certain embodiments, the cells may include Human Aortic Endothelial Cells (HAEC) or Human Umbilical Vein Endothelial Cells (HUVEC) (In-vitrogen, Carlsbad Calif.). Iron oxide (IO) nanoparticles are suited for biological testing because they have a long blood retention time, and are therefore good for MRI contrast, they are biodegradable, and they exhibit low toxicity. Briefly, cells may be labeled with IO nanocrystals (Ocean Nano-Tech, Springdale, Ark.) by incubating the nanocrystals with the cells for 2-3 h at 37° C. and allowing the cells to internalize the particles. Once the cells take up the IO particles and become magnetic, the cells are washed to remove free nanoparticles and Transmission Electron Microscopy (TEM) can be used to verify particle internalization. Magnetically labeled cells may be used immediately. Additionally, the IO nanoparticles may include a streptavidin tag that allows detection by a biotin-conjugated fluorescent antibody and separation by cell sorting. Binding pairs other than streptavidin and biotin may be substituted.

Nanostructured surfaces of biomaterials have shown to stimulate adhesion, differentiation and proliferation on a variety of human stem cells. Our results have shown that Directed Irradiation Synthesis (DIS) can mimic the nanoscale environment influencing human umbilical vein endothelial cells (HUVEC-CS). HUVEC-CS were grown on silicon (Si) wafers deposited with thin gold (Au) and palladium (Pd) films with a high cell proliferation rate and formed cell monolayers over the test material surfaces. A comparison of the toxicity and rate of DNA damage to cells grown on Au and Pd films magnetron-sputter deposited onto Si wafers to that of experimental controls showed that the Au and Pd films have low toxicity and a low incidence of DNA damage. In contrast, HUVEC-CS treated with hydrogen peroxide exhibited toxicity and DNA damage that was significantly higher than that of HUVEC-CS seeded on known biocompatible materials (PDMS, Dermafill) and Au/Si-Pd/Si wafers.

In certain embodiments, a stent of the invention may include an ion-beam nano-structured bio-compatible coating suitable for tissue proliferation to promote healing. This may be accomplished by nano-topography evolution of 100-200 nm thick gold film during irradiation by heavy-ion sputtering (e.g. Ar, Xe, etc.).

A tissue nidus is useful to repair a vascular defect across a scaffold. In vasculogenesis, there can be seen both spontaneous healing of a tiny puncture wound in arterial walls and failed vascular remodeling seen in aneurysms. To induce repair and reestablish the tunica media, an intervening homograft or allograft would be needed over the defect which would serve as the nidus to which the peripheral rim of the defect (aneurysm neck orifice) could direct its growth.

The PCSM was chosen as the nidus because PCSM cells can retain their phenotypic plasticity in culture and thus mimic in vitro their in vivo differentiation states as shown by various vascular studies.

Additionally, the arterial wall provides a source of stem cell derivatives for tunica media reconstruction. The nano-structured surfaces of the stent coating will act as a cue to guide the differentiation and proliferation of the internal stem cells.

The described embodiments above are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

Each cited reference is incorporated by reference in its entirety.

The invention claimed is:

1. A coating for improving cellular adhesion, differentiation, and proliferation for use with stents, the coating comprising:
 a layer of a magnetic material deposited on a portion of an outer surface of the stent, wherein the magnetic material comprises a bacterial nanocellulose polymer impregnated with a magnetic metal material; and
 an ion-beam nanostructured biocompatible layer deposited on the layer of magnetic material.

2. The coating of claim 1, wherein the ion-beam nanostructured biocompatible layer comprises gold.

3. The coating of claim 1, wherein the ion-beam nanostructured biocompatible layer is produced during irradiation by ion sputtering.

4. The coating of claim 1, wherein the magnetic metal material is nickel.

5. The coating of claim 1, wherein the magnetic material comprises endothelial cells.

6. The coating of claim 1 further comprising a plurality of nanoscale particles embedded in the coating to provide radiation-enhanced tomography for visualization of a stent surface.

7. The coating of claim 1 further comprising a chromium layer positioned between the layer of magnetic material and the outer surface of the stent.

8. The coating of claim 1 further comprising a bioactive layer formed on the ion-beam nanostructured biocompatible layer.

9. The coating of claim 8, wherein the bioactive layer comprises porcine coronary smooth muscle (PCSM).

10. A coating for improving cellular adhesion, differentiation, and proliferation for use with a stent, the coating comprising:
   a chromium layer deposited on an outer surface of the stent;
   a layer of a magnetic material deposited on a portion of the chromium layer, wherein the magnetic material comprises a polymer impregnated with a magnetic metal material;
   an ion-beam nanostructured biocompatible layer deposited on the layer of magnetic material; and
   a bioactive layer formed on the ion-beam nanostructured biocompatible layer.

11. The coating of claim 10, wherein the ion-beam nanostructured biocompatible layer is produced during irradiation by ion sputtering.

12. The coating of claim 10, wherein the magnetic metal material is nickel.

13. The coating of claim 10, wherein the polymer is bacterial nanocellulose.

14. The coating of claim 10, wherein the magnetic material comprises endothelial cells.

15. The coating of claim 10 further comprising a plurality of nanoscale particles embedded in the coating to provide radiation-enhanced tomography for visualization of a stent surface.

16. The coating of claim 10, wherein the bioactive layer comprises porcine coronary smooth muscle (PCSM).

* * * * *